(12) United States Patent
Shi et al.

(10) Patent No.: US 6,586,635 B2
(45) Date of Patent: Jul. 1, 2003

(54) PROCESS FOR THE PREPARATION OF UNSATURATED KETONES

(75) Inventors: Nongyuan Shi, Hanau (DE); Bernd Drapal, Alzenau (DE); Steffen Krill, Speyer (DE); Markus Julino, Hanau (DE); Klaus Huthmacher, Gelnhausen (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 10/132,195

(22) Filed: Apr. 26, 2002

(65) Prior Publication Data

US 2002/0169342 A1 Nov. 14, 2002

(30) Foreign Application Priority Data

Apr. 28, 2001 (DE) ......................................... 101 21 058

(51) Int. Cl.$^7$ ........................... C07C 45/71; C07C 45/68
(52) U.S. Cl. ...................... 568/322; 568/361; 568/405; 568/409; 568/415
(58) Field of Search ................................ 568/322, 361, 568/425, 409, 415

(56) References Cited

U.S. PATENT DOCUMENTS

| | | |
|---|---|---|
| 3,029,287 A | 4/1962 | Marbet et al. |
| 6,184,420 B1 | 2/2001 | Teles et al. |
| 6,380,437 B1 * | 4/2002 | Shi et al. |

FOREIGN PATENT DOCUMENTS

| | | |
|---|---|---|
| DE | 1 230 783 | 12/1966 |
| DE | 196 49 564 | 6/1998 |
| DE | 199 49 796 A1 | 4/2001 |
| EP | 1 092 700 | 4/2001 |

OTHER PUBLICATIONS

Synthesen des Vitamins A2 $^+$, Chimia 14, Nov. 1960; pp. 362–363.

Ueber Eine Neuartige Synthese Von Beta–Ketoallenen Durch Reaktion Von Tertiaeren Acetylencarbinolen Mit Vinylaethern Eine Ergiebige Methode Zur Darstellung Des Pseudojonons Und Verwandter Verbindungen; von G. Saucy, et al.; Helvetica Chimica Acta; vol. 50, Fascuculus 4 (1967)–No. 119; pp. 1158–1167.

Preparation of (3Z,5E)–, (3Z,5Z)–, and additional isomers of 6,10–dimethylundeca–3,5,9–triene–2–one (Abstract only), Patent No. CS 235228, May 15, 1985; Application No. CS 1982–6994, Oct. 1, 1982.

* cited by examiner

Primary Examiner—Samuel Barts
Assistant Examiner—Sikarl A. Witherspoon
(74) Attorney, Agent, or Firm—Oblon, Spivak, McClelland, Maier & Neustadt, P.C.

(57) ABSTRACT

A process for the preparation of $\beta,\gamma,\delta$-unsaturated ketones and/or $\alpha,\beta,\gamma,\delta$-unsaturated ketones by the reaction of an unsaturated alcohol with an enol ether or mixture of enol ethers, with formation of ketals as a by-product, at temperatures of from 50° C. to 200° C., in the presence of an acid catalyst, whereby one or all of the reagents is/are heated to the reaction temperature of from 50° C. to 200° C. before the acid catalyst is added.

20 Claims, No Drawings

PROCESS FOR THE PREPARATION OF UNSATURATED KETONES

BACKGROUND OF THE INVENTION

1. Field of the Invention

The present invention relates to an improved process for the preparation of $\beta,\gamma,\delta$-allenic and/or $\alpha,\beta,\gamma,\delta$-conjugated di-unsaturated ketones by the reaction of propargyl alcohols with enol ethers in the presence of an acid catalyst at elevated temperature.

2. Discussion of the Background

A range of $\beta,\gamma,\delta$- and $\alpha,\beta,\gamma,\delta$-unsaturated ketones constitute valuable intermediate products for the preparation of vitamins E, A, $K_1$ and carotinoids.

Reaction of an unsaturated alcohol and an enol ether was described for the first time by Marbet and Saucy in Chimia 14 (1960), pages 362 to 363. Methyl or ethyl is isopropenyl ether, which have boiling points of 34° C. and 61° C. respectively, are often utilized in the Saucy-Marbet reaction. The reaction temperature of the Saucy-Marbet reaction is, however, higher than the boiling points of the ethers. In order to reach the reaction temperature necessary for achieving high conversions and adequate space-time yields, the reaction is carried out either in the presence of a solvent or in solvent-free manner under pressure.

DE 1 230 783 describes a process for the preparation of polyene ketones and their isomerization products from secondary alcohols in the presence of acid catalysts such as, for example, sulfuric or phosphoric acid.

U.S. Pat. No. 3,029,287 and the publication by R. Marbet and G. Saucy, Helv. Chim. Acta (1967) 50, 1158–1167 describe a process for the preparation of $\beta,\gamma,\delta$-unsaturated ketones by the reaction of propargyl alcohols with enol ethers in the presence of an acid catalyst. The reaction times required in order to achieve complete conversion of the tertiary propargyl alcohol are, however, in excess of 15 hours according to this publication. These long reaction times necessitate high reaction volumes when the process is translated to the industrial scale, hence giving rise to high capital costs.

The reaction of dehydrolinalool with isopropenyl methyl ether catalyzed by p-toluenesulfonic acid to obtain a mixture of 6,10-dimethyl-4,5,9-undecatrien-2-one and pseudoionone isomers is disclosed in CS 235228. The reaction times required in order to achieve complete conversion of the dehydrolinalool are 17 hours at 100° C. The long reaction times are disadvantageous in this process.

It was described in DE 199 49 796.6 that the Saucy-Marbet reaction is catalyzed efficiently by aliphatic sulfonic acids or sulfonic acid salts, with markedly shortened reaction times in comparison to prior art processes. The reaction times are from 6 to 8 hours. In accordance with this process the reaction is carried out in the presence of a suitable solvent so that the necessary reaction temperature can be reached. However, yields decrease when working under pressure in the absence of the solvent. Carrying it out the process in the presence of a solvent moreover gives rise to an increased plant cost for isolating and working up the product.

SUMMARY OF THE INVENTION

Accordingly, an object of the invention is to improve the reaction between an unsaturated alcohol and an enol ether in a Saucy-Marbet reaction to obtain unsaturated ketones so as to enable the reaction to be carried out in highly selective manner and with markedly reduced reaction times. A further object of the invention is the achievement of the aforementioned aims without the need to work with additional reaction solvents.

DETAILED DESCRIPTION OF THE INVENTION

The invention provides a process for the preparation of $\beta,\gamma,\delta$-unsaturated ketones and/or $\alpha,\beta,\gamma,\delta$-unsaturated ketones by the reaction of an unsaturated alcohol with an enol ether or mixture of enol ethers, with formation of ketals as a by-product, at temperatures of from 50° C. to 200° C., in the presence of an acid catalyst.

The process according to the invention is characterized in that one or all of the reagents is/are heated to reaction temperatures of from 50° C. to 200° C. before the acid catalyst is added.

One aspect of the invention is a process for the preparation of $\beta$, $\gamma$, $\delta$ unsaturated ketones corresponding to the general Formula (IA) and/or $\alpha$, $\beta$, $\gamma$, $\delta$-unsaturated ketones corresponding to the general Formula (IB)

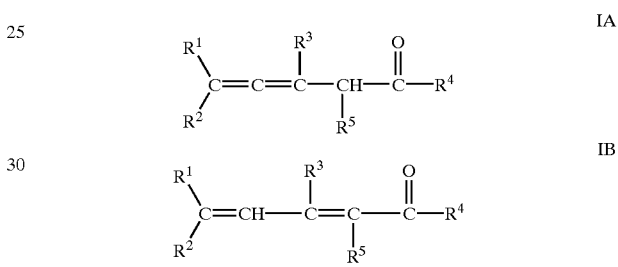

in which
$R^1$ and $R^2$ are hydrogen, a $C_1$–$C_{20}$ alkyl radical which is optionally substituted with oxygen-containing groups and may be saturated or unsaturated, branched or unbranched, or a $C_1$–$C_{20}$ alkylaryl radical, whereby the radicals $R^1$ and $R^2$ may also together form a 5- or 6-membered ring;
$R^3$ and $R^5$ are hydrogen or a $C_1$ to $C_4$-alkyl radical, preferably hydrogen, and
$R^4$ is a hydrogen or a $C_1$ to $C_4$-alkyl radical;
or mixture thereof,
by the reaction of an unsaturated alcohol corresponding to the general Formula II

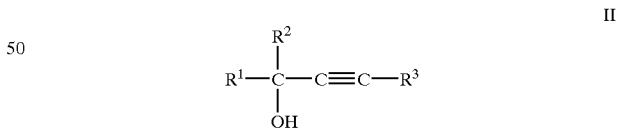

in which
$R^1$, $R^2$ and $R^3$ denote the same as indicated above, with an enol ether corresponding to the general Formula III

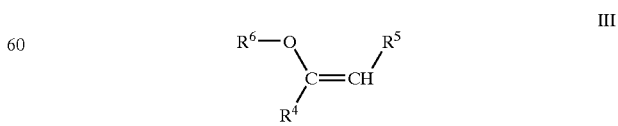

in which
$R^4$ is hydrogen or a $C_1$- to $C_4$-alkyl radical, preferably a methyl radical;

$R^5$ denotes the same as indicated above, and
$R^6$ is a $C_1$- to $C_4$-alkyl radical, preferably a methyl radical;
with formation, as a by-product, of ketals corresponding to the Formula IV in which $R^4$, $R^5$ and $R^6$ denote the same as indicated above

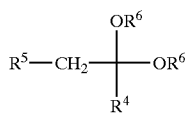

IV at temperatures of from 50° C. to 200° C., in the presence of an acid catalyst.

The process according to the invention may, for example, be carried out in the following variants:

A. an unsaturated alcohol corresponding to the Formula II is introduced into a pressure vessel as an initial charge, and heated in the absence of the acid catalyst to a temperature of between 50° C. and 200° C., preferably between 60° C. and 170° C., particularly preferably between 80° C. and 130° C. When the desired reaction temperature is reached, with the pressure having risen in the vessel, an enol ether corresponding to the Formula III or a mixture of enol ethers corresponding to the Formula III, an acid catalyst, are dispensed-in, in mixed or separate manner, in continuous manner or portion-wise; or B. an unsaturated alcohol corresponding to the Formula II as a mixture with an enol ether corresponding to the Formula III or a mixture of enol ethers corresponding to the Formula III is introduced into a pressure vessel as an initial charge, and heated in the absence of the acid catalyst to a temperature of between 50° C. and 200° C., preferably between 60° C. and 170° C., particularly preferably between 80° C. and 130° C. When the desired reaction temperature is reached, with the pressure having risen in the vessel, the acid catalyst is then dispensed-in in a continuous manner or portion-wise; or C. the enol ether corresponding to the Formula III or a mixture of enol ethers corresponding to the Formula III is introduced into a pressure vessel as an initial charge, and heated in the absence of the acid catalyst and the unsaturated alcohol to a temperature of between 50° C. and 200° C., preferably between 60° C. and 170° C., particularly preferably between 80° C. and 130° C. When the desired reaction temperature is reached, and the pressure within the vessel has increased, an acid catalyst and an unsaturated alcohol corresponding to the Formula II, are then added, in mixed or separate manner, in continuous manner or portion-wise, In each of A, B and C described above, it is possible to introduce as an initial charge, and then to heat to a temperature of between 50° C. and 200° C., a portion of the reagent or reagents in the absence of the acid catalyst, and then to add thereto the remainder of the reagent or reagents and the acid catalyst in continuous manner or portion-wise.

In a farther aspect of the invention, a liquid base or a basic solution which is able to form a salt which has acid properties "in situ" with the acid catalyst, may be added into the initial reaction mixture, in addition to the dispensing-in portion-wise or in continuous manner of the acid catalyst, at the necessary reaction temperature.

When the reaction is carried out under the conditions according to the invention only low concentrations of by-products, in particular high-boiling by-products, other than the desired ketal are formed. The ketal is a starting material for the preparation of the enol ether corresponding to the Formula III and can be recycled for this purpose. The reaction of the process according to the invention proceeds in highly selective manner, and despite high reaction rates, excellent yields are obtained, even in the absence of a solvent. Working-up in particular is substantially facilitated by the achievement of high selectivities such as, for example, at least 85%, preferably at least 90% and particularly preferably at least 93%.

The space-time yields of the process according to the invention are consequently substantially higher than those of the prior art.

Preferred unsaturated alcohols corresponding to the Formula II in the process according to the invention are those in which $R^1$ stands for a $C_1$–$C_{20}$ alkyl radical which may be saturated or unsaturated, branched or unbranched, a $C_1$–$C_{20}$ aryl radical, or an arylalkyl radical, and $R^2$ stands for a $C_1$ to $C_4$ alkyl radical, in particular a methyl radical, $R^3$ stands for hydrogen.

The following are examples of suitable propargyl alcohols:
3-methyl-1-butyn-3-ol;
3,7-dimethyl-6-octen-1-yn-3-ol (dehydrolinalool);
3,7-dimethyl-5-octen-1-yn-3-ol;
3,7-dimethyl-4-octen-1-yn-3-ol;
3,7-dimethyl-1-octyn-3-ol(hydrodehydrolinalool);
3,7,11-trimethyl-6,10-dodecadien-1-yn-3-ol (dehydronerolidol);
3,7,11-trimethyl-6-dodecen-1-yn-3-ol;
3,7,11-trimethyl-1-dodecyn-3-ol(hydrodehydronerolidol);
1-ethynyl-1-cyclohexanol; and
1-ethynyl-2,2,6-trimethyl-1-cyclohexanol.

As enol ethers corresponding to the Formula III, compounds in which
$R^4$ is hydrogen or a methyl radical,
$R^5$ is hydrogen, and
$R^6$ is a methyl radical or ethyl radical
are preferably considered.

The following are examples of suitable enol ethers: isopropenyl methyl ether, isopropenyl ethyl ether, isopropenyl propyl ether, isopropenyl butyl ether, isopropenyl isobutyl ether, 2-methoxy-1-butene, 2-ethoxy-1-butene, 2-propoxy-1-butene, 3-butoxy-1-butene, 2-m ethoxy-2-butene, 2-ethoxy-2-butene, 2-methoxy-1-pentene, 2-ethoxy-1-pentene, 2-methoxy-2-pentene, 2-ethoxy-2-pentene, 3-methoxy-3-pentene, 3-ethoxy-2-pentene, in particular isopropenyl methyl ether.

On an industrial scale isopropenyl methyl ether is frequently preferred for reasons relating to both economics and process engineering because the dimethoxypropane formed from it can be readily recovered by distillation from the reaction mixture and re-utilized for the preparation of isopropenyl methyl ether.

The reaction takes place at temperatures of between approx. 50° C. and 200° C., preferably between 60° C. and 170° C., particularly preferably between 80° C. and 130° C. A particularly high reaction rate such as, for example, less than 5 hours, preferably less than 4 hours, particularly preferably less than 3 hours, is achieved with no observable impairment of the selectivity, when the reaction is carried out at different temperature levels which are adjusted dependent on the degree of conversion of the unsaturated alcohol. At the beginning of the reaction a temperature is normally adjusted which is approximately 10° C.–30° C. lower than the temperature level at the end of the reaction.

The reaction may be carried out in a batch, semi-batch or continuous process. The reaction may furthermore be carried out in pressure-less manner but also under pressure. In the case of a pressure reaction the reaction takes place within the pressure range 1 to 20 bar, preferably 1 to 10 bar.

The molar ratio of the unsaturated alcohol corresponding to the Formula II and the enol ether corresponding to the Formula III is generally between 1:2 and 1:10, preferably 1:2.05 to 1:5, particularly preferably 1:2.05 to 1:3.5. The excess enol ether may be recovered by distillation after the reaction has ended.

The following serve as catalysts in the process according to the invention: mineral acids such as, for example, sulfuric or phosphoric acid and salts thereof, strong organic acids such as oxalic acid, trichloroacetic acid, p-toluic acid, as well as Lewis acids such as zinc chloride or boron trifluoride etherate, and aliphatic sulfonic acids and salts of the corresponding sulfonic acids having acid properties are particularly preferred.

The following are examples of suitable aliphatic sulfonic acids: methanesulfonic acid, ethanesulfonic acid, propanesulfonic acid, butanesulfonic acid, pentanesulfonic acid, hexanesulfonic acid, chloromethanesulfonic acid, in particular methanesulfonic and ethanesulfonic acid.

The following are examples of suitable sulfonic acid salts: pyridinium p-toluolsulfonate, tetramethylammonium p-toluenesulfonate, pyridinium methanesulfonate, pyridinium ethanesulfonate, in particular pyridinium p-toluolsulfonate and pyridinium methanesulfonate, which may optionally form in situ from the corresponding acid and the corresponding base.

A solvent such as acetone, methyl isobutyl ketone, methyl isopropyl ketone, ethanoic acid, formic acid, propionic acid, 2-ethylhexanoic acid may be used as a solvent for the catalysts. It is, however, also possible to utilize the unsaturated alcohol corresponding to the general Formula II, in which $R^1$ and $R^2$ denote the same as indicated above. The quantity of the solvent for the acid catalyst is not critical and is typically from 5 to 100 times the quantity of the catalyst.

The Saucy-Marbet reaction may be carried out with or without reaction solvent. Reactions which are carried out in solvent-free manner are preferred. The following may be utilized as suitable reaction solvents within the scope of the present invention: hydrocarbons, for example hexane, heptane, octane, toluene and xylene; and ketones, for example isobutyl methyl ketone, diethyl ketone isophorone, and dimethoxypropane. If utilized, the reaction solvent may be used in quantities of from 0.5 to 10 times the quantity of the propargyl alcohol utilized. The reaction may be carried out in discontinuous manner but also in continuous manner.

A cascade of stirred-tank reactors or tubular reactors designed for reactions under pressure, or a cascade of corresponding stirred-tank reactors and tubular reactors is then used as the reaction vessel.

The $\alpha,\beta,\gamma,\delta$- and $\beta,\gamma,\delta$-unsaturated ketones desired as intermediate products for vitamin E, vitamin A, carotinoids and fragrances may be prepared by the process of the invention. The product IA or mixture of IA and IB may be converted by basic isomerization to $\alpha,\beta,\gamma,\delta$-dienones corresponding to the general Formula IB, in which $R^1$, $R^2$, $R^3$ and $R^4$ denote the same as indicated above, the latter may be used as important intermediates for vitamin A, E, $K_1$ and carotinoids.

However, the allene ketones which arise may also be hydrogenated to saturated ketones corresponding to the general Formula V

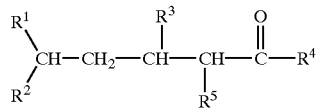

in which $R^1$, $R^2$, $R^3$ and $R^4$ denote the same as indicated above. The saturated ketones can be important intermediates for vitamin E synthesis.

The Examples which follow serve to describe specific embodiments of the invention and are not intended to limit the invention.

EXAMPLE 1

Preparation of phytone from 3,7,11-trimethyl-1-dodecin-3-ol 89.8 grams (g) 3,7,11-trimethyl-1-dodecin-3-ol (0.4 mole) and 101 g isopropenyl methyl ether (1.4 mole) are charged into a pressure vessel. The reactor is purged with nitrogen and the pressure raised to 2 bar. The educt mixture is heated to 110° C. A solution of 104 milligrams (mg) methanesulfonic acid dissolved in 45 milliliters (ml) acetone is dispensed-in portion-wise by a pump within 4 hours (h). After a total of 4.5 h 3,7,11-trimethyl-1-dodecin-3-ol is completely reacted. The autoclave is cooled to room temperature (approx. 25° C.), and the pressure is released.

The reaction mixture is neutralized by the addition of a methanolic NaOAc solution. Low-boiling components, primarily excess isopropenyl methyl ether and 2,2-dimethoxypropane, are then separated on a rotary film evaporator and condensed in a cold trap. The mixture of 6,10,14-trimethylpentanedeca-4,5-dien-2-one and 6,10,14-trimethylpentanedeca-3,5-dien-2-one, which is obtained, is hydrogenated to phytone with Pd/C catalyst. 99 g phytone are obtained, which corresponds to a total yield of 93% in relation to 3,7,11-trimethyl-1-dodecin-3-ol.

Comparative Example A

Preparation of Phytone from 3,7,11-trimethyl-1-dodecin-3-ol 78.5 g 3,7,11-trimethyl-1-dodecin-3-ol (0.35 mole) and 75.7 g isopropenyl methyl ether (1.05 mole) are charged into a pressure vessel. A solution of 54 mg methanesulfonic acid in 2 ml acetone is added to it. The reactor is purged with nitrogen and the pressure raised to 2 bar. The mixture is heated to 95° C. After 6 h a 97% conversion of 3,7,11-trimethyl-1-dodecin-3-ol is achieved.

The autoclave is cooled to room temperature, and the pressure is released. The reaction mixture is neutralized by the addition of a methanolic NaOAc solution. Low-boiling components, primarily excess isopropenyl methyl ether and 2,2-dimethoxypropane, are then separated on a rotary film evaporator and condensed in a cold trap. The mixture of 6,10,14-trimethylpentanedeca-4,5-dien-2-one and 6,10,14-trimethylpentanedeca-3,5-dien-2-one, which is obtained, is hydrogenated to phytone with a Pd/C catalyst. 79 g phytone are obtained, which corresponds to a total yield of 84% in relation to 3,7,11-trimethyl-1-dodecin-3-ol.

EXAMPLE 2

Preparation of 6,10,14-trimethylpentanedeca-4,5-dien-2-one and 6,10,14-trimethylpentanedeca-3,5-dien-2-one from 3,7,11-trimethyl-dodec-1-yn-3-ol 103 g 3,7,11-trimethyl-1-dodecin-3-ol (0.46 mole) and 99 g isopropenyl methyl ether (1.38 mole) are charged into a pressure vessel. The reactor is purged with nitrogen and the pressure raised to 2 bar. The educt mixture is heated to 90° C. A solution of 71 mg methanesulfonic acid dissolved in 60 ml acetone is dispensed-in portion-wise by a pump within 90 min. The temperature is then increased to 115° C., and stirring continues at 115° C. for 60 min. The autoclave is cooled to room temperature (approx. 25° C.), and the pressure is released. The reaction mixture is neutralized by the addition of a methanolic NaOAc solution. Low-boiling components, primarily excess isopropenyl methyl ether and 2,2-dimethoxypropane, are then separated on a rotary film evaporator and condensed in a cool trap. The residue is distilled under high vacuum. 103 g of a mixture of 6,10,14-trimethylpentanedeca-4,5-dien-2-one and 6,10,14-trimethylpentanedeca-3,5-dien-2-one are obtained. This corresponds to a yield of 85% in relation to 3,7,11-trimethyl-1-dodecin-3-ol.

EXAMPLE 3

Preparation of Phytone from 3,7,11-trimethyl-dodec-1-yn-3-ol 56.1 g 3,7,11-trimethyl-dodec-1-yn-3-ol (0.25 mole) and 63.1 g isopropenyl methyl ether (0.875 mole) are charged into a nitrogen-purged pressure vessel. The reactor is closed, and the pressure is raised with nitrogen to 2 bar. The educt mixture is heated to 95° C. A solution of 58 mg methanesulfonic acid in 7 ml acetone is dispensed-in portion-wise by a pump within 2.5 hours (h). The reaction is then held at 110° C. for a further 30 minutes (min). After a total of 3 h 3,7,11-trimethyl-dodec-1-yn-3-ol is 99% converted.

The autoclave is cooled to room temperature (approx. 25° C.), and the pressure is released. The reaction mixture is neutralized by the addition of a methanolic sodium acetate solution. Low-boiling components, primarily excess isopropenyl methyl ether and 2,2-dimethoxypropane, are then separated on a rotary film evaporator and condensed in a cold trap. The mixture of 6,10,14-trimethyl-penta-deca-4,5-dien-2-one and 6,10,14-trimethylpentanedeca-3,5-dien-2-one, which is obtained, is hydrogenated in 2-propanol to phytone with a Pd/C catalyst. 62 g phytone are obtained following the removal of the solvent. This corresponds to a total yield of 93% in relation to 3,7,11-trimethyl-dodec-1-yn-3-ol.

EXAMPLE 4

Preparation of Phytone from 3,7,11-trimethyl-dodec-1-yn-3-ol

As described in Example 1, 67.3 g 3,7,11-trimethyl-dodec-1-yn-3-ol (0.30 mole) and 75.7 g isopropenyl methyl ether (1.05 mole) are charged into a nitrogen-purged pressure vessel. The reactor is closed, and the pressure is raised with nitrogen to 2 bar. The educt mixture is heated to 80° C. A solution of 80 mg methanesulfonic acid in 10 ml acetone is dispensed-in portion-wise by a pump within 3 h. 3,7,11-trimethyl-dodec-1-yn-3-ol is 99% converted.

The autoclave is cooled to room temperature (approx. 25° C.), and the pressure is released. The reaction mixture is neutralized by the addition of a methanolic sodium acetate solution. Low-boiling components, primarily excess isopropenyl methyl ether and 2,2-dimethoxypropane, are then separated on a rotary film evaporator and condensed in a cold trap. The mixture of 6,10,14-trimethyl-pentadeca-4,5-dien-2-one and 6,10,14-trimethyl-penta-deca-3,5-dien-2-one, which is obtained, is hydrogenated in 2-propanol to phytone with a Pd/C catalyst. 74 g phytone result following the removal of the reaction solvent. This corresponds to a total yield of 92% in relation to 3,7,11-trimethyl-dodec-1-yn-3-ol.

EXAMPLE 5

Preparation of Phytone from 3,7,11-trimethyl-dodec-1-yn-3-ol 94.3 g 3,7,11-trimethyl-dodec-1-yn-3-ol (0.42 mole) and 90.9 g isopropenyl methyl ether (1.26 mole) are charged into a pressure vessel under nitrogen. The reactor is closed, and the pressure is raised with nitrogen to 2 bar. The educt mixture is heated to 90° C. A solution of 97 mg methanesulfonic acid in 12 ml acetone is dispensed-in portion-wise by a pump within 3 h. In the first hour the temperature is held at between 95° C. and 100° C., and then heated to 115° C. In parallel with the heating, 16.1 g isopropenyl methyl ether (0.23 mole) are dispensed-in by a pump within 30 min. Stirring of the mixture continues for 30 min. The 3,7,11-trimethyl-dodec-1-yn-3-ol conversion is around 99%.

Cooling takes place to room temperature (approx. 25° C.), and the pressure is released. The reaction mixture is neutralized by the addition of a methanolic sodium acetate solution. Low-boiling components, primarily excess isopropenyl methyl ether and 2,2-dimethoxypropane, are then separated on a rotary film evaporator and condensed in a cold trap. The mixture of 6,10,14-trimethyl-penta-deca-4,5-dien-2-one and 6,10,14-trimethyl-pentadeca-3,5-dien-2-one, which is obtained, is hydrogenated in 2-propanol to phytone with a Pd/C catalyst. 105 g phytone are obtained following the removal of the reaction solvent. This corresponds to a total yield of 93% in relation to 3,7,11-trimethyl-dodec-1-yn-3-ol.

EXAMPLE 6

Preparation of phytone from 3,7,11-trimethyl-dodec-1-yn-3-ol

As described in Example 3, 89.8 g 3,7,11-trimethyl-dodec-1-yn-3-ol (0.40 mole) and 57.7 g isopropenyl methyl ether (0.80 mole) are charged into a pressure vessel. The reactor is closed, and the pressure is raised with nitrogen to 2 bar. The educt mixture is heated to 95° C. A solution of 66 mg methanesulfonic acid in 8 ml acetone is dispensed-in portion-wise by a pump within 2.5 h. In the first 45 minutes the temperature is held at between 95 and 100° C., and then heated to 115° C. In parallel with the heating, 14.4 g isopropenyl methyl ether (0.20 mole) are dispensed-in within 20 minutes. The 3,7,11-trimethyl-dodec-1-yn-3-ol conversion is around 99%.

Cooling takes place to room temperature (approx. 25° C.), and the pressure is released. The reaction mixture is neutralized by the addition of a methanolic sodium acetate solution. Low-boiling components, primarily excess isopropenyl methyl ether and 2,2-dimethoxypropane, are then separated on a rotary film evaporator and condensed in a cold trap. The mixture of 6,10,14-trimethyl-penta-deca-4,5-dien-2-one and 6,10,14-trimethyl-penta-deca-3,5-dien-2-one, which is obtained, is hydrogenated in 2-propanol to phytone with Pd/C catalyst. 99.2 g phytone are obtained. This corresponds to a total yield of 93% in relation to 3,7,11-trimethyl-dodec-1-yn-3-ol.

EXAMPLE 7

Preparation of Tetrahydrogeranyl Acetone from 3,7-dimethyl-oct-1-yn-3-ol 231.4 g 3,7-dimethyl-oct-1-yn-3-ol (1.50 mole) and 324.5 g isopropenyl methyl ether (4.50 mole) are charged into a pressure vessel under nitrogen. The reactor is closed, and the pressure is raised with nitrogen to 2 bar. The educt mixture is heated to approx. 90° C. A solution of 265 mg methanesulfonic acid in 16 ml acetone is dispensed-in portion-wise by a pump within 1.5 h. Stirring is continued for 30 min at 90–92° C. The 3,7-dimethyl-oct-1yn-3-ol conversion is around 99%.

The mixture is cooled to room temperature (approx. 25° C.), and the pressure is released. The reaction mixture is neutralized by the addition of a small quantity of triethylamine. Low-boiling components, primarily excess isopropenyl methyl ether and 2,2-dimethoxypropane, are then separated on a rotary film evaporator and condensed in a cold trap. The mixture of 6,10-dimethyl-undeca-4,5-dien-2-one and 6,10-dimethyl-undeca-3,5-dien-2-one, which is obtained, is hydrogenated in 2-propanol to tetrahydrogeranyl acetone with a Pd/C catalyst. 271 g tetrahydrogeranyl acetone are obtained. This corresponds to a total yield of 91% in relation to 3,7-dimethyl-oct-1-yn-3-ol.

EXAMPLE 8

Preparation of Tetrahydrogeranyl Acetone from 3,7-dimethyl-oct-1-yn-3-ol 216.0 g 3,7-dimethyl-oct-1-yn-3-ol (1.40 mole) and 324.5 g isopropenyl methyl ether (4.50 mole) are charged into a pressure vessel under nitrogen. The reactor is closed, and the pressure is raised with nitrogen to 2 bar. The educt mixture is heated to 85° C. A solution of 234 mg methanesulfonic acid in 16 ml 3,7-dimethyl-oct-1-yn-3-ol is dispensed-in portion-wise by a pump within 1.5 h. Stirring is continued for 30 min at 90–92° C. The 3,7-dimethyl-oct-1-yn-3-ol conversion is around 99%.

Cooling takes place to room temperature (approx. 25° C.), and the pressure is released. The reaction mixture is neutralized by the addition of 3.0 ml of a methanolic sodium acetate solution (0.10 g/ml). Low-boiling components, primarily excess isopropenyl methyl ether and 2,2-dimethoxypropane, are then separated on a rotary film evaporator and condensed in a cold trap. The mixture of 6,10-dimethyl-undeca-4,5-dien-2-one and 6,10-dimethyl-undeca-3,5-dien-2-one, which is obtained, is hydrogenated in 2-propanol to tetrahydrogeranyl acetone with Pd/C catalyst. 273 g tetrahydrogeranyl acetone are obtained. This corresponds to a total yield of 92% in relation to 3,7-dimethyl-oct-1-yn-3-ol.

EXAMPLE 9

Preparation of tetrahydrogeranyl acetone from 3,7-dimethyl-oct-1-yn-3-ol 77.2 g 3,7-dimethyl-oct-1-yn-3-ol (0.50 mole) and 108.2 g isopropenyl methyl ether (1.50 mole) are charged into a pressure vessel under nitrogen. The reactor is closed, and the pressure is raised with nitrogen to 2 bar. The educt mixture is heated to 90° C. 9.0 ml of a solution of 403 mg sulfuric acid in 50 ml acetone are dispensed-in portion-wise within 1.5 h. After continued stirring for 1.5 h at 90–95° C. a 99% conversion is obtained. The autoclave is cooled to room temperature, and the pressure is released. The reaction mixture is neutralized by the addition of 1.5 ml of a methanolic sodium acetate solution (0.10 g/ml). Low-boiling components, primarily excess isopropenyl methyl ether and 2,2-dimethoxypropane, are then separated on a rotary film evaporator and condensed in a cold trap. The mixture of 6,10-dimethyl-undeca-4,5-dien-2-one and 6,10-dimethyl-undeca-3,5-dien-2-one, which is obtained, is hydrogenated in 2-propanol to tetrahydrogeranyl acetone with a Pd/C catalyst. The solvent is separated on a rotary film evaporator and condensed in a cold trap. 90 g tetrahydrogeranyl acetone are obtained. This corresponds to a total yield of 91% in relation to 3,7-dimethyl-oct-1-yn-3-ol.

EXAMPLE 10

Preparation of Tetrahydrogeranyl Acetone from 3,7-dimethyl-oct-1-yn-3-ol 77.2 g 3,7-dimethyl-oct-1-yn-3-ol (0.50 mole) and 101 g isopropenyl methyl ether (1.40 mole) are charged into a pressure vessel under nitrogen. The reactor is closed, and the pressure is raised with nitrogen to 2 bar. The educt mixture is heated to 90° C. A solution of 96 mg methanesulfonic acid in 12 ml acetone is dispensed-in portion-wise by a pump within 1.5 h. In parallel with the heating, a solution of 330 mg pyridine in 9.6 ml isopropenyl methyl ether is pumped-in portion-wise. Stirring continues for 1.5 h following the addition of the acid catalyst. The 3,7-dimethyl-oct-1-yn-3-ol conversion is around 99%.

Cooling to room temperature (approx. 25° C.) takes place, and then the pressure is released. A small quantity of pyridine is added to the reaction mixture. Working-up then proceeds as described above. The mixture of 6,10-dimethyl-undeca-4,5-dien-2-one and 6,10-dimethyl-undeca-3,5-dien-2-one, which is obtained, is hydrogenated in 2-propanol to tetrahydrogeranyl acetone with a Pd/C catalyst. 92 g tetrahydrogeranyl acetone are obtained. This corresponds to a total yield of 93% in relation to 3,7-dimethyl-oct-1-yn-3-ol.

EXAMPLE 11

Preparation of Tetrahydrogeranyl Acetone from 3,7-dimethyl-oct-1-yn-3-ol 77.2 g 3,7-dimethyl-oct-1-yn-3-ol (0.50 mole) and 108.2 g isopropenyl methyl ether (1.50 mole) are charged into a pressure vessel under nitrogen. The reactor is closed, and the pressure is raised with nitrogen to 2 bar. The educt mixture is heated to 90° C. 14.8 ml of a solution of 602 mg p-toluenesulfonic acid in 50 ml acetone are dispensed-in portion-wise by a pump within 1.5 h. Stirring takes place for 120 minutes at 90–95° C., cooling takes place to room temperature, and the pressure is released. The reaction mixture is neutralized by the addition of a small quantity of triethylamine. Low-boiling components, primarily excess isopropenyl methyl ether and 2,2-dimethoxypropane, are then separated on a rotary film evaporator and condensed in a cold trap. The mixture of 6,10-dimethyl-undeca-4,5-dien-2-one and 6,10-dimethyl-undeca-3,5-dien-2-one, which is obtained, is hydrogenated in 2-propanol to tetrahydrogeranyl acetone with Pd/C catalyst. The solvent is separated on a rotary film evaporator and condensed in a cold trap. 91 g tetrahydrogeranyl acetone are obtained. This corresponds to a total yield of 92% in relation to 3,7-dimethyl-oct-1-yn-3-ol.

Obviously, numerous modifications and variations of the present invention are possible in light of the above teachings. It is therefore to be understood that within the scope of the appended claims, the invention may be practiced otherwise than as specifically described herein.

German application 10121058.2 filed on Apr. 28, 2001 is incorporated herein by reference in its entirety.

What is claimed is:

1. A process for preparing one or more $\beta,\gamma,\delta$-unsaturated ketones and/or one or more $\alpha,\beta,\gamma,\delta$-unsaturated ketones, said process comprising reacting at least one unsaturated alcohol with at least one enol ether in the presence of an acid catalyst at a temperature of from 50° C. to 200° C., to form said unsaturated ketones and one or more ketals, wherein said unsaturated alcohol and/or said enol ether is heated to a reaction temperature of from 50° C. to 200° C. before said acid catalyst is added.

2. The process according to claim 1, wherein the β,γ,δ-unsaturated ketones are of Formula (IA) and the α,β,γ,δ-unsaturated ketones are of Formula (IB)

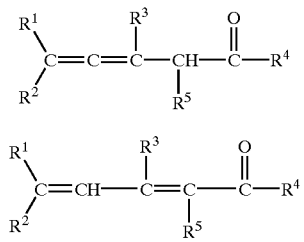

in which
each of $R^1$ and $R^2$ may be hydrogen, a $C_1$–$C_{20}$ alkyl radical which may be substituted with oxygen-containing groups and may be saturated or unsaturated, branched or unbranched, or a $C_1$–$C_{20}$ alkylaryl radical, wherein the radicals $R^1$ and $R^2$ together may form a 5- or 6-membered ring;
each of $R^3$ and $R^5$ may be hydrogen or a $C_1$ to $C_4$-alkyl radical; and
$R^4$ may be a $C_1$ to $C_4$ alkyl radical.

3. The process according to claim 1, wherein the unsaturated alcohol is of Formula II

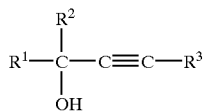

in which
each of $R^1$ and $R^2$ may be hydrogen, a $C_1$–$C_{20}$ alkyl radical which may be substituted with oxygen-containing groups and may be saturated or unsaturated, branched or unbranched, or a $C_1$–$C_{20}$ alkylaryl radical, wherein the radicals $R^1$ and $R^2$ together may form a 5- or 6-membered ring; and
$R^3$ may be hydrogen or a $C_1$ to $C_4$-alkyl radical.

4. The process according to claim 1, wherein the enol ether is of Formula III

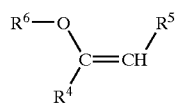

in which
$R^4$ may be hydrogen or a $C_1$- to $C_4$-alkyl radical,
$R^5$ may be hydrogen or a $C_1$- to $C_4$-alkyl radical, and
$R^6$ may be a $C_1$- to $C_4$-alkyl radical.

5. The process according to claim 4, wherein $R^4$ is a methyl radical, $R^5$ is a hydrogen atom, and $R^6$ is a methyl or ethyl radical.

6. The process according to claim 1, wherein the ketals are of Formula IV in which

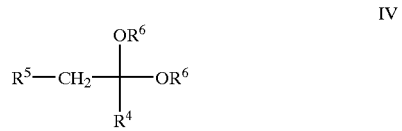

$R^4$ may be a $C_1$- to $C_4$-alkyl radical,
$R^5$ may be hydrogen or a $C_1$- to $C_4$-alkyl radical, and
$R^6$ may be a $C_1$- to $C_4$-alkyl radical.

7. The process according to claim 6, wherein $R^4$ is a methyl radical, $R^5$ is a hydrogen atom, and $R^6$ is a methyl or ethyl radical.

8. The process according to claim 1, wherein the acid catalyst is selected from the group consisting of a mineral acid, a salt of a mineral acid having acid properties, an organic acid, a Lewis acid, an aliphatic sulfonic acid, a salt of an aliphatic sulfonic acid having acid properties and mixtures thereof.

9. The process according to claim 8, wherein the mineral acid is selected from the group consisting of sulfuric acid, phosphoric acid, a salt of sulfuric acid having acid properties, a salt of phosphoric acid having acidic properties and mixtures thereof.

10. The process according to claim 8, wherein the organic acid is oxalic acid, trichloroacetic acid or p-toluic acid.

11. The process according to claim 8, wherein the Lewis acid is zinc chloride, or boron trifluoride etherate.

12. The process according to claim 8, wherein the acid catalyst is in solution with a solvent.

13. The process according to claim 12, wherein the solvent is selected from the group consisting of acetone, methyl isobutyl ketone, methyl isopropyl ketone, ethanoic acid, formic acid, propionic acid, 2-ethylhexanoic acid, the unsaturated alcohol of Formula II and mixtures thereof.

14. The process according to claim 8, wherein the acid catalyst is fed portion-wise or in continuous manner into the reaction.

15. The process according to claim 1, wherein the acid catalyst is methanesulfonic acid or ethanesulfonic acid.

16. The process according to claim 1, wherein no reaction solvent is present.

17. The process according to claim 1, wherein a reaction solvent is present.

18. The process according to claim 17, wherein the reaction solvent is selected from the group consisting of hexane, heptane, octane, toluene, xylene, isobutyl methyl ketone, diethyl ketone, isophorone, dimethoxypropane and mixtures thereof.

19. The process according to claim 1, wherein the reaction temperature is from 60° C. to 170° C.

20. The process according to claim 1, wherein the reaction temperature is from 80° C. to 130° C.

* * * * *